US005835188A

United States Patent [19]

Moreno

[11] Patent Number: 5,835,188

[45] Date of Patent: Nov. 10, 1998

[54] DEVICE FOR EXERCISING THE EXTRINSIC EYE MUSCLES

[76] Inventor: Gil G. Moreno, 4106 Dellbrook Dr., Tampa, Fla. 33624

[21] Appl. No.: 722,555

[22] Filed: Sep. 27, 1996

[51] Int. Cl.[6] .......... A61B 3/00

[52] U.S. Cl. .......... 351/203; 351/200

[58] Field of Search .......... 351/203, 200, 351/222, 224, 226, 225

[56] References Cited

U.S. PATENT DOCUMENTS

| | | | |
|---|---|---|---|
| 3,774,599 | 11/1973 | Martin | 128/76.5 |
| 3,843,240 | 10/1974 | Cornsweet | 351/2 |
| 3,875,934 | 4/1975 | Sadanaga | 128/76.5 |
| 4,402,580 | 9/1983 | Ross | 351/203 |
| 4,408,846 | 10/1983 | Balliet | 351/203 |
| 4,464,027 | 8/1984 | Cooper | 351/203 |
| 4,506,963 | 3/1985 | Cooper | 351/203 |
| 4,804,262 | 2/1989 | Katsuhiko et al. | 351/226 |
| 4,838,677 | 6/1989 | Bronskill | 351/203 |
| 4,854,690 | 8/1989 | Mehr | 351/203 |
| 4,940,323 | 7/1990 | Downing | 351/203 |
| 5,040,888 | 8/1991 | Bonham | 351/203 |
| 5,422,688 | 6/1995 | Asea | 351/203 |
| 5,520,543 | 5/1996 | Mitui | 434/236 |
| 5,534,953 | 7/1996 | Schmielau | 351/203 |

*Primary Examiner*—Hung X. Dang

[57] ABSTRACT

This relates to a device to be located in front of a person eyes containing a plurality of light sources disposed and mounted near the edge, and on the concave side of a dish shaped wall. The position of said dish shaped wall relative to the user eyes and visual axis is adjustable by means adjustable forhead and chin supports. Each individual light source is sequentially turned on and off. When one light source turns off the following light source turns on immediately or after a predetermined time delay. The sequence may be clockwise, counterclockwise, zig-zag, random or any desired pattern. The person using this invention must move his eyes to focus them on the light source that turns on sequentially.

6 Claims, 7 Drawing Sheets

DEVICE FOR EXERCISING THE EXTRINSIC EYE MUSCLES

BACKGROUND OF THE INVENTION

It has long been recognized that great benefit is derived from exercising the eye muscles. It makes good sense to exercise the eyes muscles after they have been used in close work for a long time as it is to exercise the leg muscles after sitting in a cramped position.

The eye can be moved in any direction by six extrinsic muscles, approximately 50 degrees up, 35 degrees down, 45 degrees out, and 50 degrees toward the nose. With the increase use of computer monitors and television sets the eye movement have been greatly reduced. The eyes move only approximately 3 degrees up and down and approximately 3 degrees outward and toward the nose when viewing the computer monitor, because the viewer move the head instead of the eyes. The eyes move approximately 10 degrees up and down and outward and toward the nose when viewing a television show. During reading, the eyes practically do not move because the reader moves the head instead of the eyes. It is obvious that this condition for an extended period of time may induce eye muscles atrophy.

An old way to exercise the eye muscles was to look at a point on a picture frame and then follow the frame of the picture with the eyes. The main difficulty of this method is that it requires a great deal of mental effort in order to follow an imaginary point on the picture frame. The person using this method wants to finish as soon as possible.

U.S. Pat. No. 5,422,688 has the disadvantage that the eyes muscles do not exercise to their maximum angular capacity.

U.S. Pat. No. 3,774,599 has the disadvantage of being electromechanical and complicated for exercising the six extrinsic eye muscles.

No practical device is known for exercising the six extrinsic eye muscles that is portable, effective, lightweight, and that does not require too much mental effort during its use.

SUMMARY OF THE INVENTION

The principal object of the present invention is to provide a device to exercise the six extrinsic eye muscles that is portable, effective, lightweight, and that require minimum mental effort.

It is also an object of the present invention to provide a device which is of inexpensive construction.

Another object of the present invention is to provide a device that is attractive and pleasant to use.

A further object is to provide a device which will contribute to a healthy vision.

For accomplishing these objects a plurality of light sources are disposed and mounted on a circular wall. Preferably said wall is shaped like a dish and said light sources are disposed on the concave side on points of one or more curved and closed lines parallel to the edge of said dish shaped wall to project the light emitted, outwardly from the concave side. Said plurality of light sources may be in a plane or in different planes. Said dish shaped wall of approximately nine inches diameter is to be located in front of a viewer eyes with its concave surface facing the eyes. By locating said light sources near the edge of said dish shaped wall, the light emitted by said light sources are aimed toward the viewer eyes. Instead of circular, said wall may be elliptical or of any other shape and instead of dish shaped, it may be a flat wall. Each individual light source is sequentially turned on and off. When a light source turns off, the following light source turns on immediately or after a predetermined time delay. The sequence may be clockwise, counterclockwise, random or any desired pattern. Said dish shaped wall has a back cover with a handle. Said back cover is shaped like a bowl. Said back cover is disposed to embrace said dish shaped wall with its open end extending in front of said dish shaped wall to shield the viewer from external lighting. Said back cover has posts perpendicular to its bottom inner surface to support said dish shaped wall. Said posts are used to fasten said dish shaped wall to said back cover and to provide an space between the inner surface of said back cover bottom and the convex surface of said dish shaped wall to house electronic circuitry and electric battery.

The eye exercising device is provided with adjustable forehead and chin supports. These supports are disposed to allow adjustment of the distance between the dish shaped wall and the eyes in the direction of the visual axis. Also the supports allow adjustment of the dish shaped wall up and down in a plane perpendicular to the visual axis.

The person using this invention must move his eyes to focus them on the light source that turns on sequentially.

DESCRIPTION OF THE PREFERRED EMBODIMENTS

Figure 1:
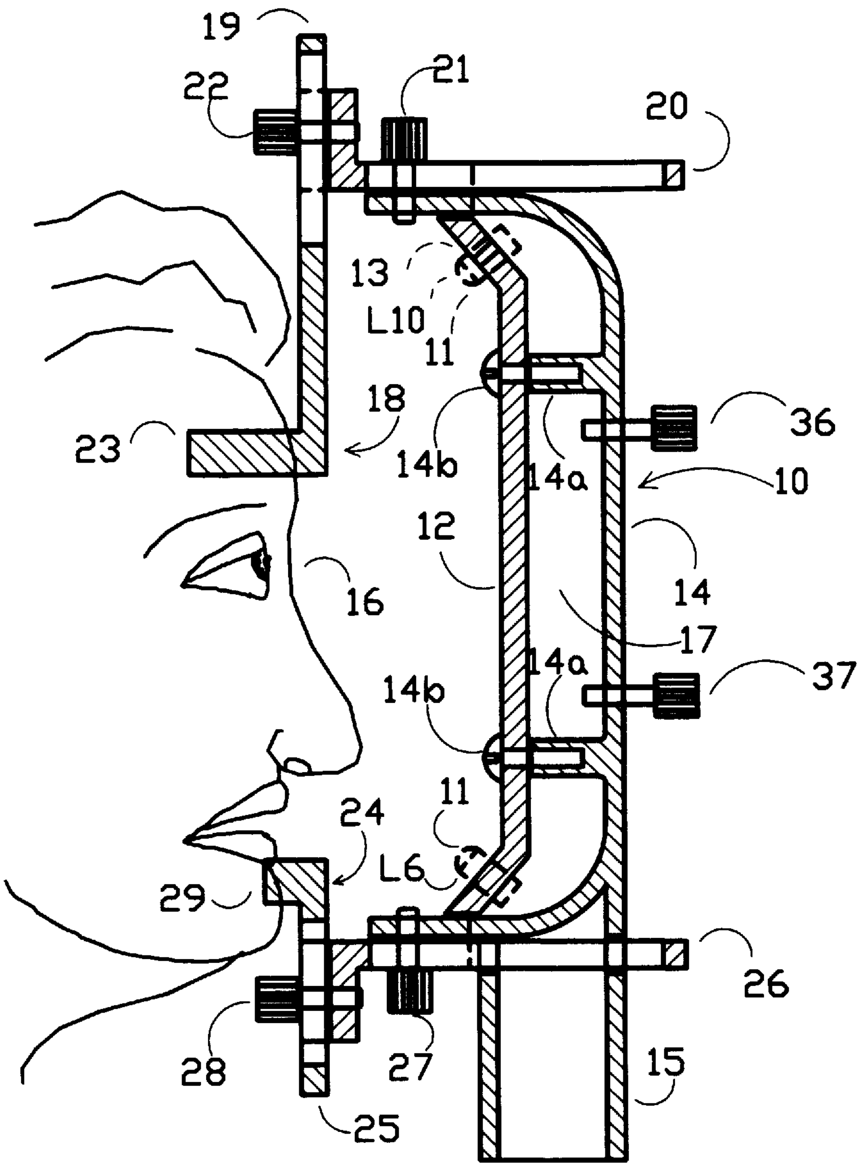
FIG. 1 is a cross-sectional view of the apparatus for exercising the eye muscles.
Figure 2:
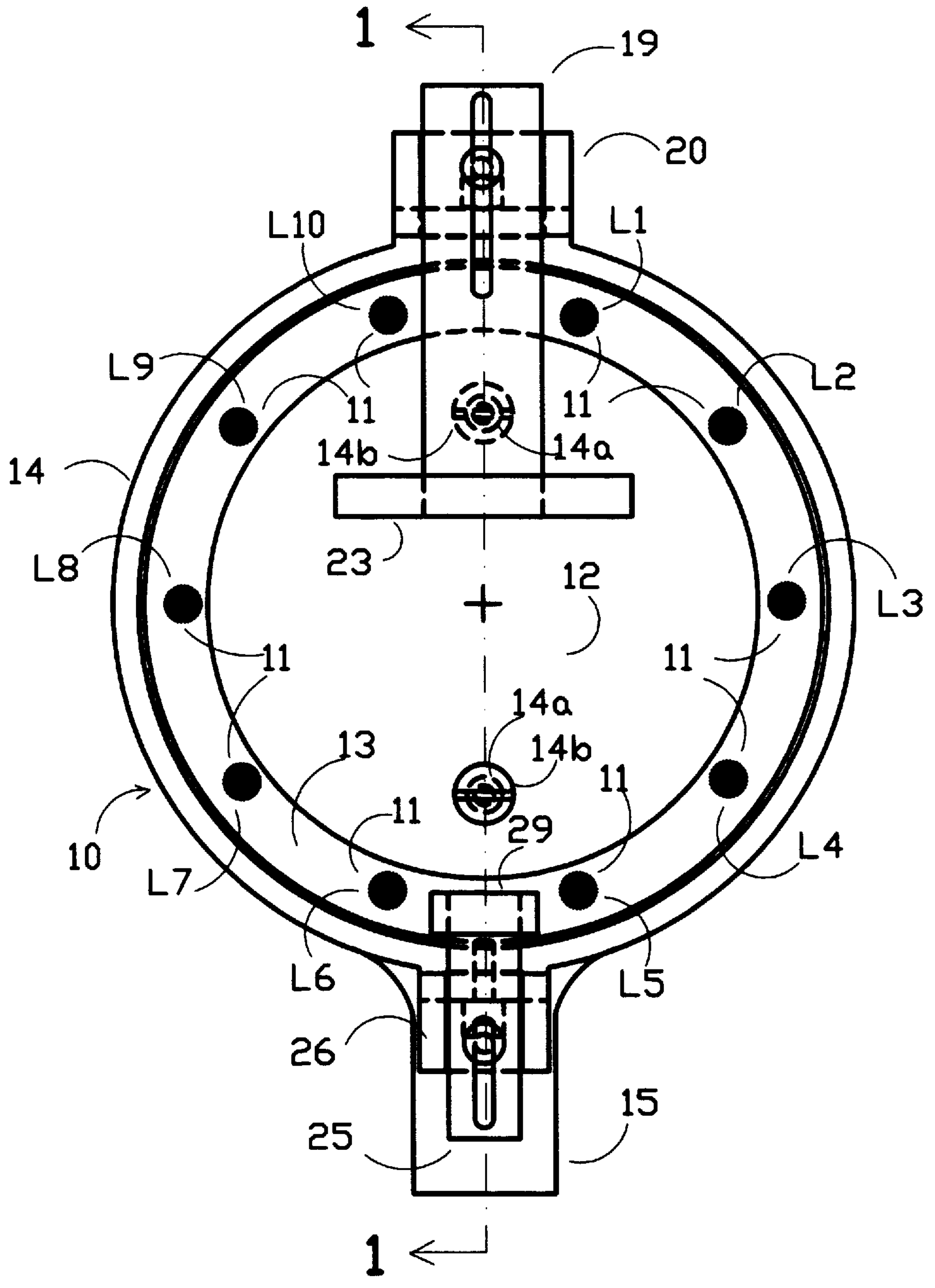
FIG. 2 is a front elevated view of the apparatus for exercising the eye muscles.
Figure 3:
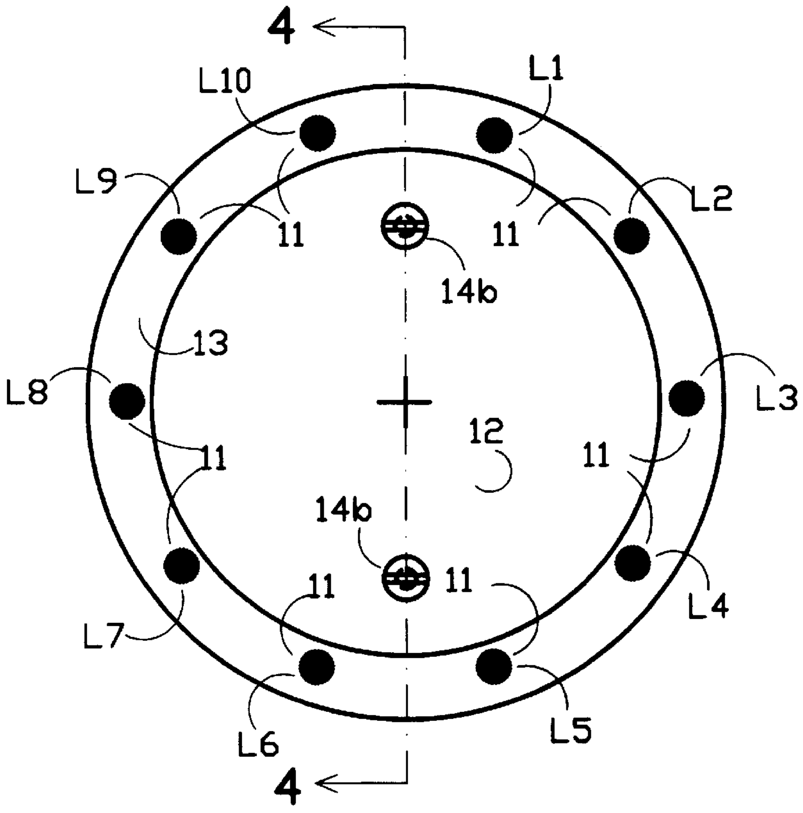
FIG. 3 is a front elevated view of the dish shaped wall of the eye exercising apparatus.
Figure 4:
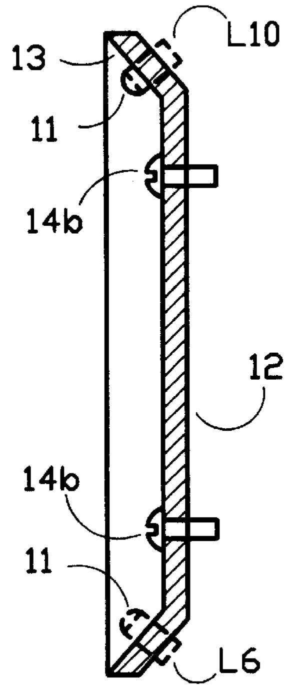
FIG. 4 is a cross-sectional view of the dish shaped wall of the eye exercising apparatus.
Figure 5:
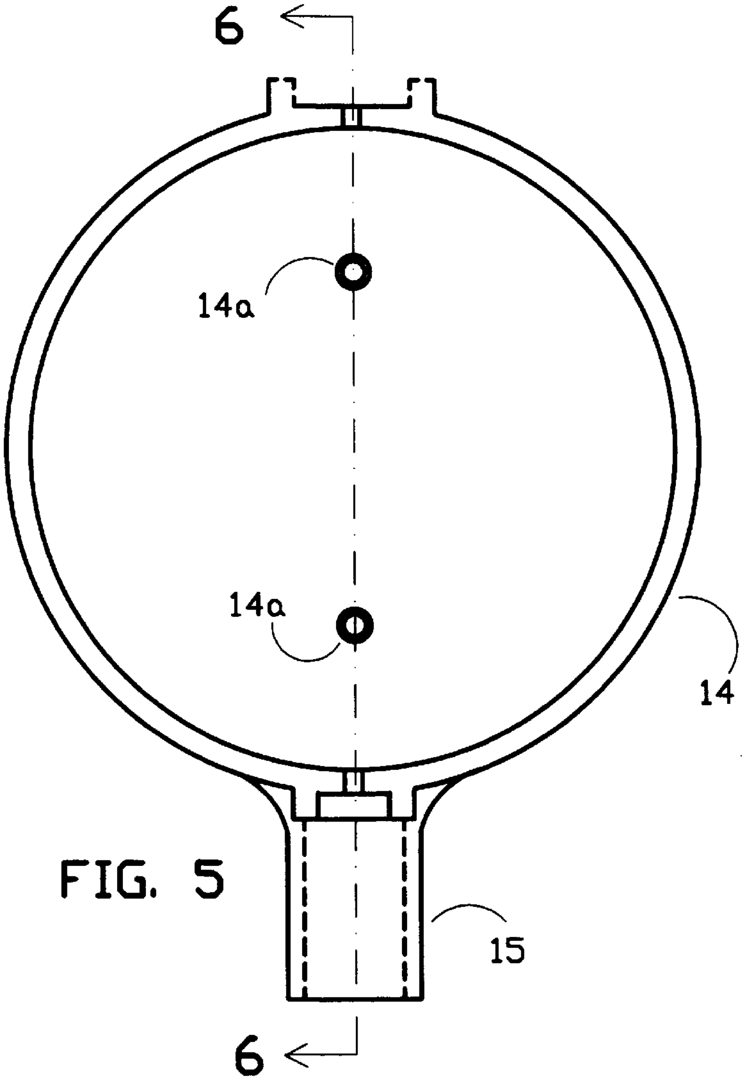
FIG. 5 is a front elevated view of the back cover and handle of the eye exercising apparatus.
Figure 6:
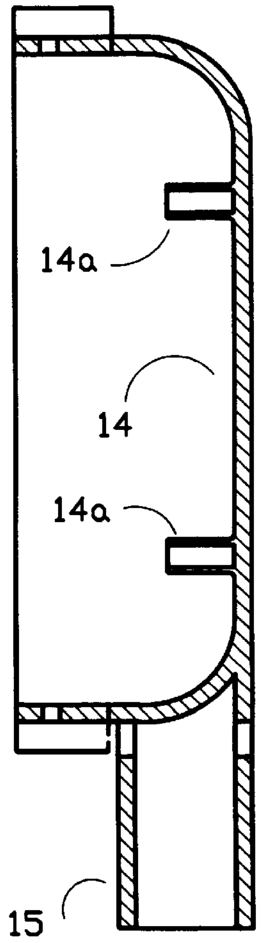
FIG. 6 is a cross-sectional view of the back cover and handle of the eye exercising apparatus.
Figure 7:
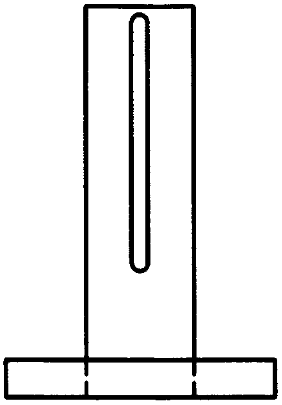
FIGS. 7 through 12 are views of the two arms of the forehead support.
Figure 8:
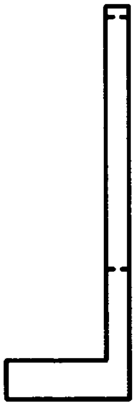
Figure 10:
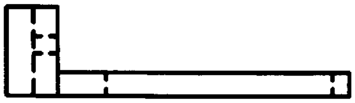
Figure 11:
Figure 12:
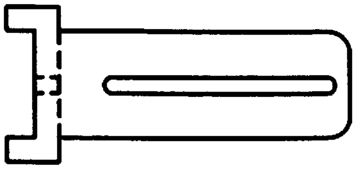
Figure 9:
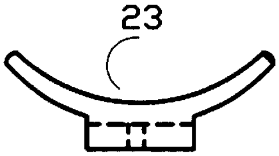
Figure 13:
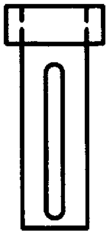
FIGS. 13 through 18 are views of the two arms of the chin support.
Figure 14:
Figure 16:
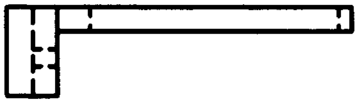
Figure 17:
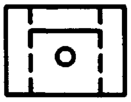
Figure 18:
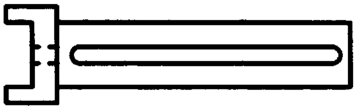
Figure 15:

Referring to FIGS. 1 through 18 the eye exerciser device generally designated 10, has ten light emitting diodes L1, L2, L3, L4, L5, L6, L7, L8, L9, and L10 as light sources 11, disposed and mounted on the concave side of a dish shaped wall 12 near its edge 13. Said dish shaped wall 12 is to be positioned in front of a viewer eyes 16 with its concave side facing said viewer eyes 16. Said dish shaped wall 12 has a back cover 14 shaped like a bowl. Said back cover 14 has a handle 15 for holding the device in front of said viewer eyes 16. The open end of said back cover 14 extend in front of said dish shaped wall 12 to shield the viewer from external lighting. Post 14*a*, projecting away from the inner surface of said back cover 14, are used to fasten said dish shaped wall 12 to said back cover 14 and to create an space 17 between said dish shaped wall 12 and said back cover 14. Said space 17 is used to house electronic circuitry and battery that power and control said light sources 11. Screws 14*b* are used to fasten said dish shaped wall 12 to said back cover 14. Said light sources 11 are turned on and off sequentially. The sequence may be clock-wise, counter clock-wise, random or any desired sequence. When one of said light sources 11 turns off, the following light source 11 turns on immediately or after a predetermined time delay.

Adjustable forehead support generally designated 18 has a first and second arm 19 and 20. Said arm 20 is disposed to engage with said back cover 14 and is secured to it by screw 21. Said arm 19 is disposed to engage with said arm 20 and is secured to it by screw 22. Said arm 19 has a forhead seat 23 shaped to conform with the forehead curvature. Adjustable chin support generally designated 24 has a first and second arm 25 and 26. Said arm 26 is disposed to engage with said back cover 14 and is secured to it by screw 27. Said arm 25 is disposed to engage with said arm 26 and is secured to it by screw 28. Said arm 25 has a chin seat 29 shaped to conform with the chin curvature. Said adjustable forehead support 18 and said chin support 24 are disposed to allow adjustment of the distance between said dish shaped wall 12 and said viewer eyes 16 and align the center of said dish shaped wall 12 with the visual axis of the viewer.

Figure 19:
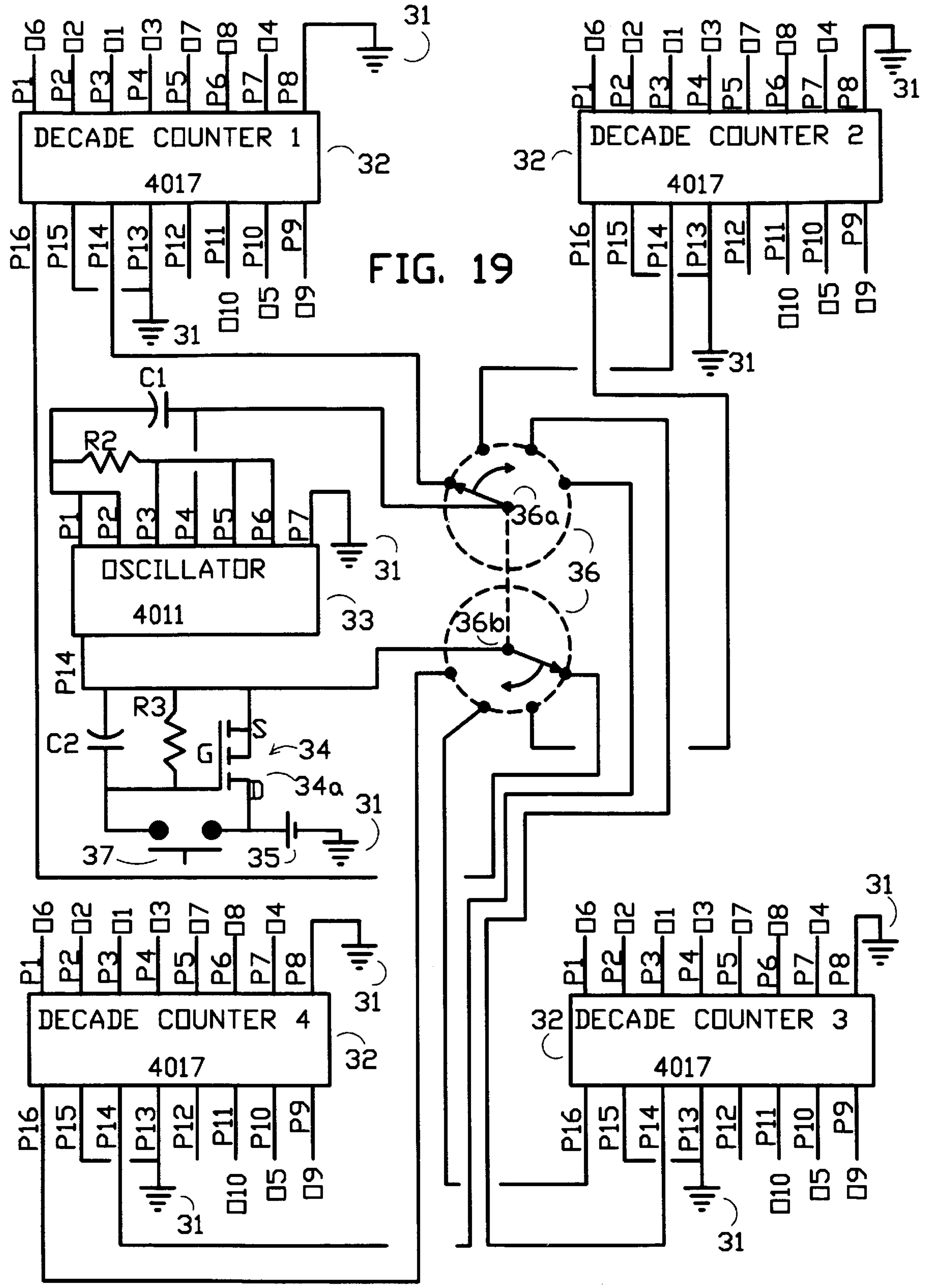
FIGS. 19 and 19A are the schematic diagrams of the electronic circuitry that powers and controls the light sources.
Figure 19A:
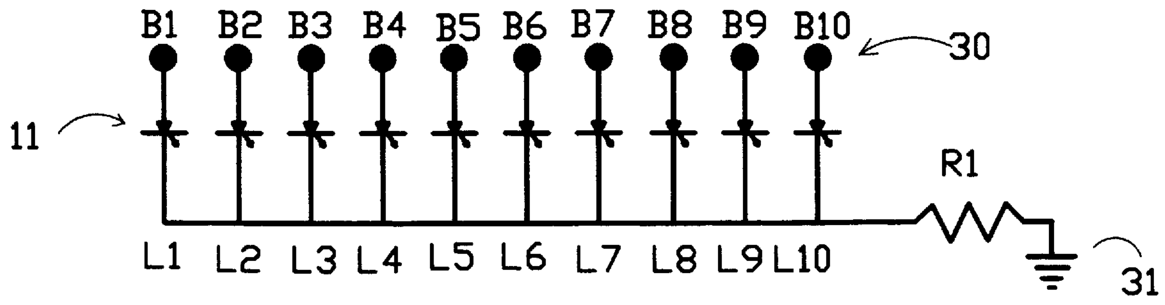

Referring to FIGS. 19 and 19A, light emitting diodes L1, L2, L3, L4, L5, L6, L7, L8, L9, and L10 have their anodes electrically connected to electric conductive buses B1, B2, B3, B4, B5, B6, B7, B8, B9, and B10 respectively. Electric conductive buses B1, B2, B3, B4, B5, B6, B7, B8, B9, and B10 are generally designated 30. Electric paths are provided from the cathodes of all light sources 11 to ground 31. Decade counters typically number 4017 generally designated 32 have ten decoded outputs O1, O2, O3, O4, O5, O6, O7, O8, O9 and O10. When an output turns high the preceding output turns low and remains low until the end of the cycle. Electric paths are provided in said decade counters to count from one to ten and recycle.

Electric paths are provided from the outputs of decade counter 1 to buses 30 in accordance with table No. 1, for a clock-wise sequence of ten light sources 11. When a light source 11 is turned off the following light source 11 is turned on almost immediately.

TABLE No. 1

(Decade counter 1)

| Decade counter Output | Bus |
|---|---|
| O1 | B! |
| O2 | B2 |
| O3 | B3 |
| O4 | B4 |
| O5 | B5 |
| O6 | B6 |
| O7 | B7 |
| O8 | B8 |
| O9 | B9 |
| O10 | B10 |

Electric paths are provided from the outputs of decade counter 2 to buses 30 in accordance with Table No. 2, for a counter clock-wise sequence of ten light sources 11. When a light source 11 turns off the following light source 11 turns on almost immediately.

TABLE No. 2

(Decade counter 2)

| Decade counter Output | Bus |
|---|---|
| O1 | B1 |
| O2 | B10 |
| O3 | B |

TABLE No. 2-continued (Decade counter 2)

| Decade counter Output | Bus |
|---|---|
| O4 | B8 |
| O5 | B7 |
| O6 | B6 |
| O7 | B5 |
| O8 | B4 |
| O9 | B3 |
| O10 | B2 |

Electric paths are provided from the outputs of decade counter 3 to buses 30 in accordance with Table No. 3, for a clock-wise sequence of five light sources 11. When a light source 11 turns off the following light source 11 will turns on after a predetermined time delay.

TABLE No. 3

(Decade counter 3)

| Decade counter Output | Bus |
|---|---|
| O1 | B1 |
| O2 | Not connected |
| O3 | B3 |
| O4 | Not connected |
| O5 | B5 |
| O6 | Not connected |
| O7 | B7 |
| O8 | Not connected |
| O9 | B9 |
| O10 | Not connected |

Electric paths are provided from the outputs of decade counter 4 to buses 30 in accordance with Table No. 4, for a counter clock-wise sequence of five light sources 11. When a light source 11 turns off the following light source 11 turns on after a predetermined time delay.

TABLE No. 4

(Decade counter 4)

| Decade counter output | Bus |
|---|---|
| O1 | B1 |
| O2 | Not connected |
| O3 | B9 |
| O4 | Not connected |
| O5 | B7 |
| O6 | Not connected |
| O7 | B5 |
| O8 | Not connected |
| O9 | B3 |
| O10 | Not connected |

Electric paths are provided from pin 8 of all decade counters 32 to ground 31. Electric paths are provided from pin 13 and pin 15 of all decade counter 32 to ground 31, for count recycle operation.

Quad two-input nand gate typically number 4011 is used to provide a simple oscillator generally designated 33. Frequency of oscillator 33 is adjusted by means of resistor R2 and capacitor C1.

OFF after delay switch 34 uses an N-channel MOSFET transistor typically IRF511 designated 34*a*. The time delay of said switch 34 is adjusted by means of resistor R3 and capacitor C2.

Battery 35 provides the power for the time delay switch 34, the oscillator 33 and all decade counters 32. Said battery 35 may be of the recharchable type. Means to recharge in-place the recharchable battery may be provided.

Two pole four position rotary selector switch 36 is of the break before make type. Pole 1 is designated 36*a* and pole 2 is designated 36*b*. Electric path is provided between pole 1 of said rotary selector switch 36 and the output of said oscillator 33. Electric paths are provided respectively from positions 1 through 4 of pole 1 to pin 14 of decade counters 1 through 4. Electric paths are provided from terminal S of the N-channel MOSFET transistor 34*a* to pin 14 of said oscillator 33 and to pole 2 of said rotary selector switch 36. Electric paths are provided respectively from position 1 Through 4 of pole 2 to pin 16 of decade counters 1 through 4.

When push button 37 is depressed momentarily capacitor C2 is charged through parallel internal impedances of oscillator 33 and that of the decade counter selected through pole 2 of rotary selector switch 36. The N-channel MOSFET transistor 34*a* becomes conductive energizing oscillator 33 and the decade counter selected by pole 2 of said rotary selector switch 36. The N-channel MOSFET transistor 34*a* remains conductive until the capacitor C2 discharges through resistor R3 and the internal impedance of said transistor 34*a*.

The present disclosure contains that contained in the appended claims as well as that of the foregoing description. Although the invention has been disclosed in its preferred form with a certain degree of particularity, it is understood that the invention of the preferred form has been made by way of example, that numerous changes in the details of construction and the combination and arrangement of parts may be resorted to without departing from the spirit and scope of the invention.

What is claimed is:

1. A device for exercising the eye muscles comprising in combination:

a circular dish shaped wall;

a plurality of light sources disposed and mounted on the concave side of said dish shaped wall on one or more closed curved lines near the edge and parallel to it;

an electronic circuitry that control said plurality of light sources each individual light source is sequentially turn on and off, when one light source turn off the following light source turn on;

an electric battery;

an space between the convex side of said dish shaped wall and the inner surface of said back cover bottom to house said electronic circuitry and battery;

an adjustable forehead support;

an adjustable chin support.

2. A device as set forth in claim 1 wherein said plurality of light sources turn ON and OFF sequentially in a clock-wise direction without time delay between the OFF and ON states.

3. A device as set forth in claim 1 wherein said plurality of light sources turn ON and OFF sequentially in a counter clock-wise direction without time delay.

4. A device as set forth in claim 1 wherein said plurality of light sources turn ON and OFF sequentially in a clock-wise direction with a time delay between the OFF and the ON states.

5. A device as set forth in claim 1 wherein said plurality of light sources turn ON and OFF sequentially in a counter clock-wise direction with a time delay between the OFF and ON states.

6. A device as set forth in claim 1 wherein said electronic circuitry incorporates an OFF after delay switch to energize said electronic circuitry.

* * * * *